US00PP37502P2

(12) United States Plant Patent
Mathey

(10) Patent No.: US PP37,502 P2
(45) Date of Patent: Jun. 30, 2026

(54) ***BUDDLEIA* PLANT NAMED 'SMNBWXPP'**

(50) Latin Name: ***Buddleia weyeriana* x *davidii***
Varietal Denomination: SMNBWXPP

(71) Applicant: Spring Meadow Nursery Inc, Grand Haven, MI (US)

(72) Inventor: Megan M. Mathey, Holland, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 19/370,909

(22) Filed: Oct. 28, 2025

(51) Int. Cl.
*A01H 6/00* (2018.01)
*A01H 5/00* (2018.01)

(52) U.S. Cl.
USPC ..... Plt./242

(58) Field of Classification Search
USPC ..... Plt./226, 242
See application file for complete search history.

(56) References Cited

U.S. PATENT DOCUMENTS

PP28,796 P3 * 12/2017 Wood ..... Plt./242

* cited by examiner

*Primary Examiner* — Karen M Redden

(57) ABSTRACT

A new and distinct cultivar of *Buddleia* plant named 'SMNBWXPP' is disclosed, characterized by unique flower panicles that are somewhat globular and also conical in shape. Flower petals are colored lavender in the bud stage, maturing to soft lavender and finally cream-colored. Flower throats are bright orange. Flowers have a sweet, honey-like fragrance. Plants are very dwarf and very compact with large, dark green leathery foliage. The new cultivar is a *Buddleia*, typically produced as an outdoor ornamental plant.

2 Drawing Sheets

Figure 1:
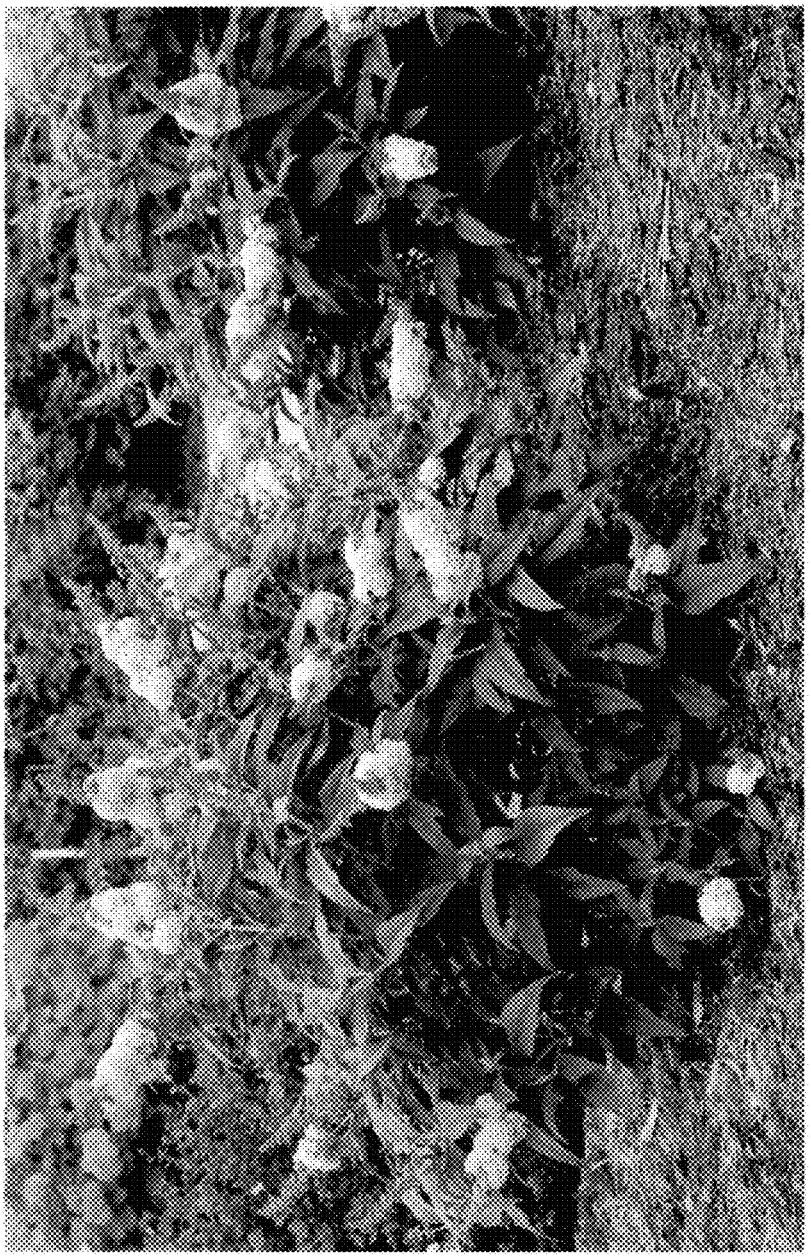

Latin name of the genus and species: *Buddleia weyeriana* x *davidii.*

Cultivar denomination: 'SMNBWXPP'.

BACKGROUND OF THE INVENTION

The new cultivar is a product of a planned breeding program conducted by the inventor to produce *Buddleia weyeriana* and *Buddleia davidii* hybrids to incorporate novel flower colors, forms and other "wild-type" characteristics into a compact form. The crossing resulting in the new cultivar was made in summer of 2017 at a nursery in Grand Haven, Michigan.

The seed parent is the unpatented cultivar *Buddleia weyeriana*, the species itself. The pollen parent is the cultivar *Buddleia davidii* 'SMNBDL', U.S. Plant Pat. No. 30,236. The new cultivar was found and selected by the inventor in summer of 2019 at the same nursery in Grand Haven, Michigan. Asexual reproduction of the new cultivar 'SMNBWXPP' was first performed during summer of 2019 in Grand Haven, Michigan, by softwood cuttings. Through subsequent propagation, multiple additional generations have been reproduced, having shown that the unique features of this cultivar are stable and reproduced true to type.

SUMMARY OF THE INVENTION

The cultivar 'SMNBWXPP' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNBWXPP'. These characteristics in combination distinguish 'SMNBWXPP' as a new and distinct *Buddleia* cultivar:

1. Foliage is dark green with broad, leathery leaves.
2. Panicles are densely packed and conical like *Buddleia davidii.*
3. Panicles exhibit the globular shape characteristic of *Buddleia weyeriana*, though slightly less defined.
4. Flower (petal) color is a soft lavender which is most vibrant on newly opened buds.
5. Flower (petal) color ages to cream, lending the inflorescence a bi-color appearance when contrasting old with newly opened flowers.
6. Flower throats are a bright burnt orange color characteristic of *Buddleia weyeriana.*
7. Plant's mature habit is very compact/dwarf with short internodes.

PARENT COMPARISONS

Plants of 'SMNBWXPP' are similar to plants of the seed parent in most horticultural characteristics, however, plants of 'SMNBWXPP' differ in the following:

1. Mature habit of the new cultivar is very compact/dwarf with short internodes, while the mature habit of the seed parent is more upright and not dwarf.
2. Flower panicles of the new cultivar exhibit some of the globular shape characteristic of *Buddleia weyeriana*, though slightly less defined. Flower panicles of the seed parent are entirely globular in shape, typical of *Buddleia weyeriana.*
3. Petal color of the new cultivar ranges from lavender to cream; throats are a bright burnt orange. Petal color of the seed parent is yellow-orange; throats are a bright burnt orange.

Plants of 'SMNBWXPP' are similar to plants of the pollen parent in most horticultural characteristics, however, plants of 'SMNBWXPP' differ in the following:

1. Petal color of the new cultivar ranges from lavender to cream; throats are a bright burnt orange. Petal color of the pollen parent is yellow-orange; throats are a bright burnt orange.
2. Flower panicles of the new cultivar are densely packed and conical but with some of the globular attributes of *Buddleia weyeriana*. Flower panicles of the pollen parent are densely packed and conical as typical of straight *Buddleia davidii*.

COMMERCIAL COMPARISONS

Plants of 'SMNBWXPP' can be compared to plants of the commercial cultivar *Buddleia davidii* 'SMNBDO', U.S. Plant Pat. No. 28,796. Plants of 'SMNBWXPP' are similar to plants of 'SMNBDO' in most horticultural characteristics, however, plants of 'SMNBWXPP' differ in the following:

1. Petal color of the new cultivar ranges from lavender to cream; throats are a bright burnt orange. Petal color of this comparator is purplish-pink; throats are medium yellow.
2. Flower panicles of the new cultivar are densely packed and conical but with some of the globular attributes of *Buddleia weyeriana*. Flower panicles of this comparator are densely packed and conical.

Plants of 'SMNBWXPP' can be compared to plants of the commercial cultivar *Buddleia weyeriana* 'Bicolor', unpatented. Plants of 'SMNBWXPP' are similar to plants of 'Bicolor' in most horticultural characteristics, however, plants of 'SMNBWXPP' differ in the following:

1. Petal color of the new cultivar ranges from lavender to cream; throats are a bright burnt orange. Petal color of this comparator ranges from lavender to apricot/peach; throats are a bright burnt orange.
2. Plants of the new cultivar are shorter at maturity than plants of this comparator.
3. Plant habit of the new cultivar is dwarf and compact, while the plant habit of this comparator is upright.

BRIEF DESCRIPTION OF THE PHOTOGRAPHS

The accompanying photograph in FIG. 1 illustrates in full color two typical plants of 'SMNBWXPP' grown outdoors in Grand Haven, Michigan. Plants are approximately 3 years old.

Figure 2:
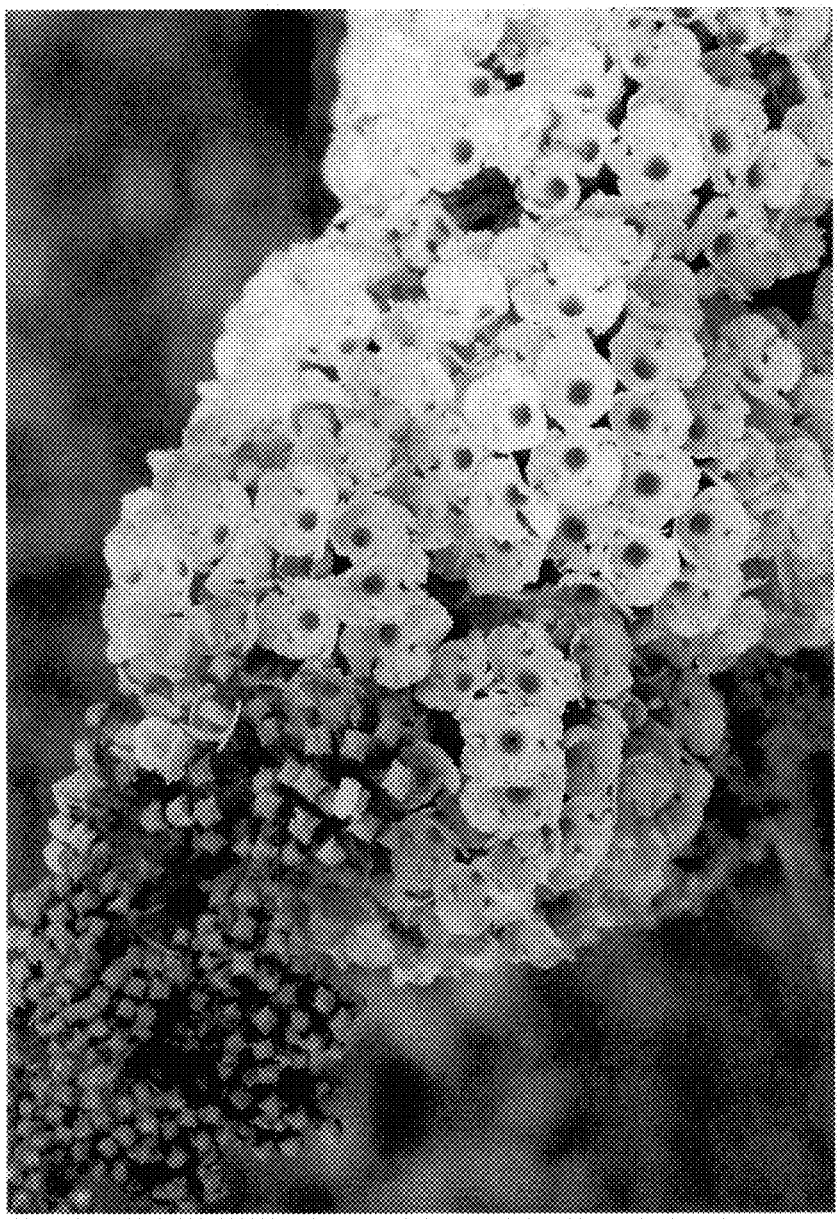

FIG. 2 illustrates in full color a close up of an inflorescence of 'SMNBWXPP'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe 'SMNBWXPP' plants grown in a poly-greenhouse in Grand Haven, Michigan. The plants were 3 years old. Temperatures ranged from 5° C. to 10° C. at night to 18° C. to 27° C. during the day. No artificial light, photoperiodic treatments were given to the plants. Measurements and numerical values represent averages of typical plant types.

Botanical classification: *Buddleia weyeriana* x *davidii* 'SMNBWXPP'.

PROPAGATION

Typical method: Softwood cuttings.

Root initiation: 14 to 21 days in summer at approximately 25° C.

Time to produce rooted cutting: About 30 days in summer at approximately 25° C.

Roots: Dense, freely branching, medium thickness, fibrous. White in color, not accurately measured with R.H.S. chart.

PLANT

Plant type: Perennial flowering shrub.
Growth habit: Compact, rounded.
Shape: Globose.
Height: 60 cm.
Plant spread: 70 cm.
Pot size of plant described: 3 gallon.
Age of plant described: 2 to 3 years.
Stem:

*Branching.*—Basal and lateral.
*Pinching.*—Some required to encourage well-rounded habit.
*Number of lateral branches.*—20 to 25.
*Shape.*—Square.
*Color.*—Immature: RHS Yellow-Green 144A with dense, Greyed-Green 195B pubescence. Mature: Near RHS Grey-Brown 199C.
*Length.*—30 cm.
*Width.*—4 mm.
*Aspect.*—0° to 45° from vertical.
*Strength.*—Moderate to high.
*Texture.*—Pubescent.
*Internode length.*—3 cm.

FOLIAGE

Leaf:

*Arrangement.*—Opposite, single.
*Shape.*—Narrowly elliptic to oblong.
*Length.*—10 cm.
*Width.*—3 cm.
*Apex.*—Acuminate.
*Base.*—Cuneate.
*Margin.*—Serrulate.
*Texture of top surface.*—Pubescent, soft; somewhat coriaceous.
*Texture of bottom surface.*—Pubescent, soft; somewhat coriaceous.
*Pubescence.*—Yes, both sides.
*Color.*—Young Foliage, Upper Side: RHS Yellow-Green 147A with a light dusting of Greyed-Green 195B pubescence. Young Foliage, Under Side: RHS Greyed-Green 195B. Mature Foliage, Upper Side: RHS Yellow-Green 147A with a light dusting of Greyed-Green 195B pubescence. Mature Foliage, Under Side: RHS Greyed-Green 195B.

Venation:
*Type*.—Pinnate.
*Color*.—Mature, Upper Side: RHS Greyed-Green 195B. Mature, Under Side: RHS Greyed-Green 195B.

Petiole:
*Length*.—5 mm.
*Width*.—2 mm.
*Color*.—Upper Side: RHS Greyed-Green 195B. Under Side: RHS Greyed-Green 195B.
*Texture*.—Upper Side: Pubescent. Under Side: Pubescent.

FLOWER

Natural flowering season: Summer.
Flower arrangement: Inflorescence.
Flowering habit: Terminal inflorescences.
Inflorescence type: Panicle.
Inflorescence shape: Inflorescence shape is a blend between the conical *Buddleia davidii* shape and the globular *Buddleia weyeriana* (formerly *B. globose*) shape.
Height: 13 cm.
Diameter: 4 cm.
Quantity of flowers per inflorescence: 150.
Quantity of buds per inflorescence: 750.
Quantity of flowers and buds per inflorescence:
Quantity of inflorescences per plant: About 20.
Quantity of flowers and buds per plant: About 15,000.
Fragrance: Sweet and floral, honey-like; moderate intensity.

Flower:
*Type or form*.—Salverform.
*Aspect*.—Outward.
*Length*.—1.1 cm.
*Diameter*.—9 mm.
*Depth*.—9 mm.
*Persistence*.—Persistent.
*Longevity*.—About 1 week.

Bud:
*Length*.—8 mm.
*Diameter*.—1 mm.
*Shape*.—Oblong with a flared, square tip.
*Color*.—RHS Purple-Violet N82C, Purple-Violet N82B at tip.

Petals:
*Number*.—4.
*Arrangement*.—Cruciform.
*Shape*.—Hemispherical.
*Tip*.—Obtuse.
*Base*.—Fused.
*Margin*.—Irregularly and shallowly serrulate.
*Length*.—4 mm.
*Width*.—4 mm.
*Texture*.—Upper side: Soft and silky. Under side: Soft and silky.
*Color*.—When Opening, Upper Side: RHS Purple-Violet N82C. When Opening, Under Side: RHS Purple-Violet N82C. Fully Opened, Upper Side: RHS Purple-Violet N82C. Fully Opened, Under Side: RHS Purple-Violet N82C. Fading, Upper Side: Near RHS Orange-White 159C. Fading, Under Side: Near RHS Orange-White 159C. Throat Color: RHS Greyed-Red 181D. Tube Color: RHS Orange 26A.

Sepals:
*Number*.—4.
*Arrangement*.—Whorl; narrowly deltate; fairly inconspicuous.
*Shape*.—Triangular.
*Tip*.—Acute.
*Base*.—Fused.
*Margin*.—Entire.
*Length*.—0.5 mm.
*Width*.—0.5 mm.
*Texture*.—Upper side: Glabrous. Under side: Glabrous.
*Color*.—Mature, Upper Side: RHS Green 138A. Mature, Under Side: RHS Green 138A.

Calyx:
*Shape*.—Oblong, with narrow, triangular sepals.
*Length*.—3 mm.
*Diameter*.—1 mm.

Peduncle:
*Terminal length*.—11 cm.
*Terminal diameter*.—3 mm.
*Angle*.—0° from vertical.
*Strength*.—High.
*Texture*.—Pubescent.
*Color*.—RHS Yellow-Green 144A with dense, Greyed-Green 195B pubescence.

Pedicel:
*Length*.—1 cm.
*Diameter*.—1 mm.
*Angle*.—45° from vertical.
*Strength*.—Medium.
*Texture*.—Pubescent.
*Color*.—RHS Yellow-Green 144A with dense, Greyed-Green 195B pubescence.

REPRODUCTIVE ORGANS

Stamens:
*Number*.—4.
*Filament length*.—No filament, anthers fused directly to interior of throat.

Anthers:
*Shape*.—Linear.
*Length*.—1 mm.
*Color*.—RHS Yellow 4D.
*Pollen amount*.—Moderate.
*Pollen color*.—RHS Yellow 4D.

Pistil:
*Number*.—1.
*Length*.—2 mm.

Stigma:
*Shape*.—Linear.
*Color*.—RHS Yellow-Green 144B.
*Style length*.—1 mm.
*Style color*.—RHS Yellow-Green 144B.
*Ovary color*.—RHS Yellow-Green 144B.

OTHER CHARACTERISTICS

Fruit and seed: Not observed.
Disease resistance: Resistance and susceptibility to typical diseases and pests of *Buddleia* not observed.
Drought tolerance and cold tolerance: Hardy to USDA Zones 5 to 9.

What is claimed is:

1. A new and distinct cultivar of *Buddleia* plant named 'SMNBWXPP' as herein illustrated and described.

* * * * *